United States Patent
Whitney et al.

[11] 4,235,234
[45] Nov. 25, 1980

[54] SUBCUTANEOUS INJECTION SYSTEM

[76] Inventors: Douglass G. Whitney, 2518 W. Wesley Rd.; John K. Martin, III, 2837 Ridge Wood Cir., both of Atlanta, Ga. 30327

[21] Appl. No.: 964,953

[22] Filed: Nov. 30, 1978

[51] Int. Cl.³ .............................................. A61M 5/00
[52] U.S. Cl. .................................... 128/216; 128/221
[58] Field of Search ............... 128/260, 216, 215, 221, 128/214 R, 253

[56] References Cited
U.S. PATENT DOCUMENTS

| | | | |
|---|---|---|---|
| 2,402,306 | 6/1946 | Turkel | 128/214 R |
| 3,863,631 | 2/1975 | Baldwin | 128/214 R |
| 3,957,048 | 5/1976 | Jacobs | 128/214 R |
| 3,964,482 | 6/1976 | Gerstel et al. | 128/260 |

Primary Examiner—John D. Yasko
Attorney, Agent, or Firm—B. J. Powell

[57] ABSTRACT

A subcutaneous injection system for injecting fluids in the subcutaneous fat layer of a patient including an injection needle having a sharpened end thereon for penetrating the subcutaneous fat layer of the patient and a locator pad carrying the needle with the locator pad having a locating surface to lie against the patient's skin from which the sharpened end of the needle projects a prescribed distance while oriented generally normal to the locating surface to positively control the depth of penetration of the sharpened end of the injection needle into the subcutaneous fat layer of the patient.

6 Claims, 10 Drawing Figures

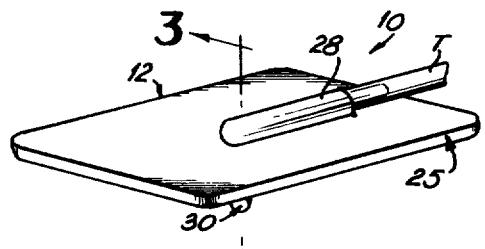
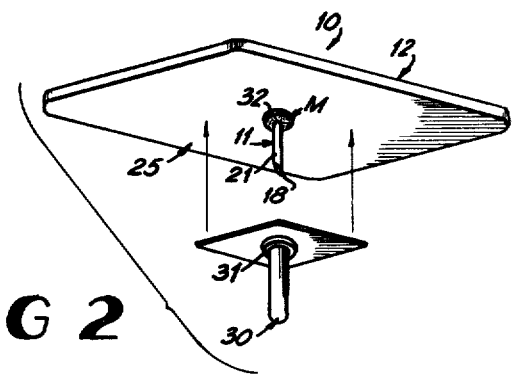
FIG 1  FIG 2
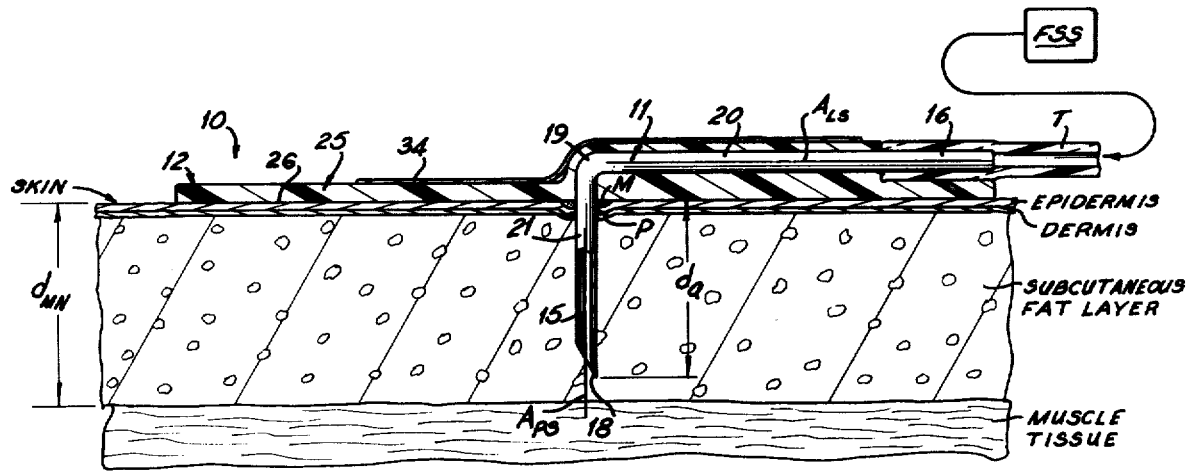
FIG 3
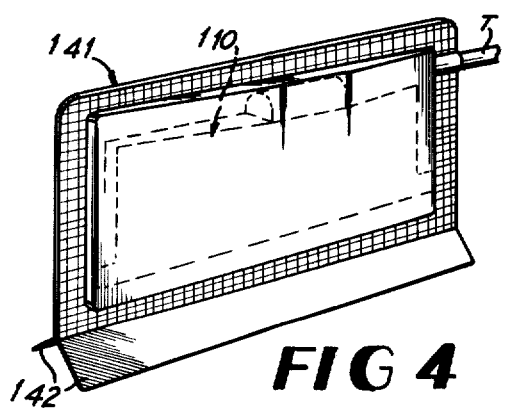
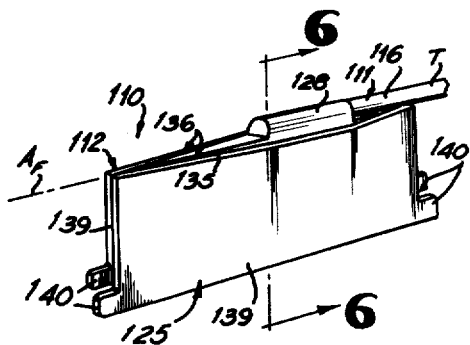
FIG 4  FIG 5

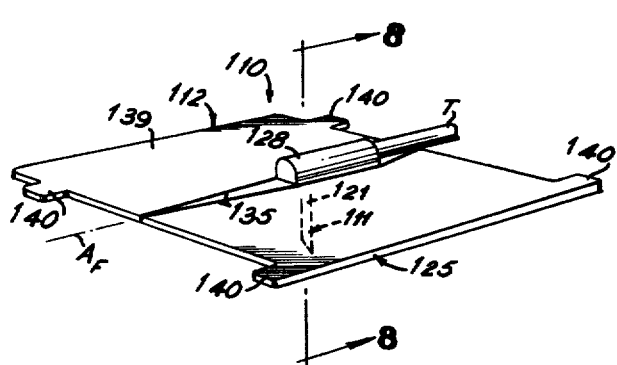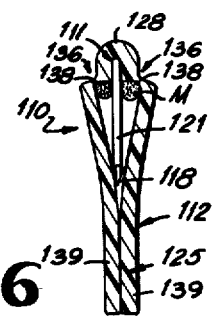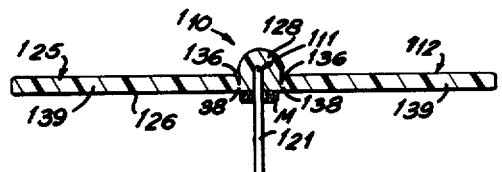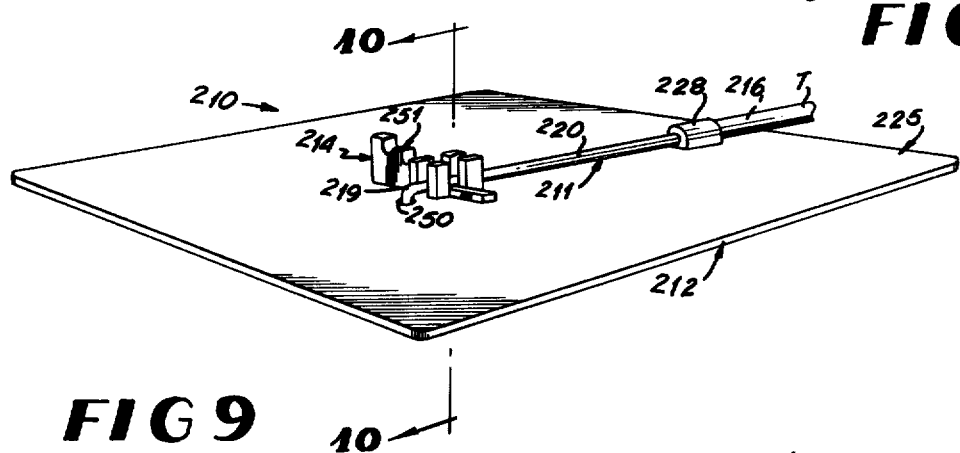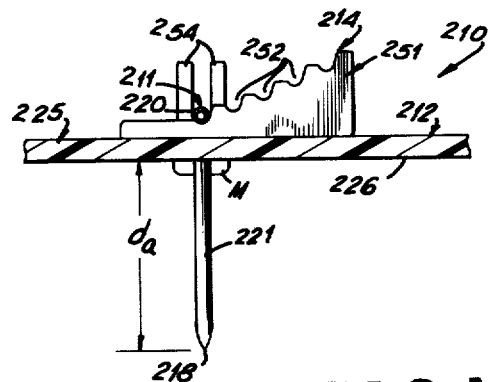

SUBCUTANEOUS INJECTION SYSTEM

BACKGROUND OF THE INVENTION

It is frequently desirable to inject fluids into the subcutaneous fat layer of a patient. This has generally been done in the past using an intravenous type injection needle assembly. However, problems have been encountered when the intravenous type needle assemblies have been used to subcutaneously inject fluids into a patient. These problems reside in the fact that these injection needle assemblies, when used for the subcutaneous injection, have been difficult to locate properly for the injection and difficult to maintain the proper position for injection once the proper location was initially achieved. In subcutaneous injection, the fluid must be injected within the subcutaneous fat layer between the patient's skin and muscle. Inasmuch as it is desirable to inject the fluid as deep as possible into the subcutaneous fat layer to isolate the point of injection of the fluid from any skin surface irritation created by the injection needle puncturing the skin, it has been difficult for the medical personnel installing these injection needle assemblies to assure that the point of injection was always sufficiently deep in the subcutaneous fat layer to be isolated from skin irritation without sometimes penetrating the muscle. This is because the thickness of the subcutaneous fat layer varies widely and because no physical limit is provided on these prior art injection needle assemblies to limit the depth of penetration.

SUMMARY OF THE INVENTION

These and other problems and disadvantages of the prior art are overcome by the invention disclosed herein by providing a means by which the point of injection can be positively located in the subcutaneous fat layer in a patient to insure that the injection point is isolated from the skin puncture yet the muscle tissue is not penetrated to provide the desired subcutaneous injection.

According to the invention, there is provided apparatus for injecting fluids from a fluid supply source into the subcutaneous fat layer of a patient below the skin without penetrating muscle tissue comprising an injection needle for connection to the fluid supply source with a sharpened outlet end adapted to puncture the patient's skin and subcutaneous fat layer; locator means mounting the needle and defining a locating surface thereon adapted to lie against the patient's skin where the sharpened outlet end of the needle projects from the locating surface a prescribed distance and is oriented generally normal thereto to positively control the depth of penetration of the sharpened end of the needle into the subcutaneous fat layer of the patient when the locating surface is in juxtaposition with the patient's skin. The needle may include a locating section adjacent its inlet end and a penetrating section adjacent the sharpened outlet end oriented generally normal to the locating section with the locating section mounted on the locator means so that the locating section is generally parallel to the locating surface and so that the penetrating section projects from the locating surface generally normal thereto. A needle cover means is provided for selectively covering the penetrating section of the needle prior to use to maintain the penetrating section of the needle sterile. The needle cover means may be incorporated in the locator means by constructing the locator means so that it is foldable about a fold axis generally coaxial with the locating section of the needle whereby those portions of the location means on opposite sides of the fold axis can be folded over the penetrating section of the needle to cover it or alternatively unfolded from around the penetrating section of the needle to expose it for use. An antimicrobal substance may be preformed around the penetrating section of the needle so that the antimicrobal substance is placed in operative cooperation with the puncture in the patient's skin made by the needle. The locator means may further include penetration adjustment means for selectively changing the prescribed distance that the sharpened outlet end of the needle projects from the locating surface.

Also, according to the invention, there is provided a method of subcutaneously injecting fluids into the subcutaneous fat layer of a patient comprising the steps of positively locating an injection needle with a sharpened end thereon with respect to a locating surface so that the sharpened end of the needle projects from the locating surface a prescribed distance slightly less than the minimum distance between the skin surface and the interface between the subcutaneous fat layer and the muscle tissue in the patient likely to be encountered at the position where subcutaneous injection is to take place, and so that the sharpened end of the needle is oriented generally normal to the locating surface, then inserting the sharpened end of the needle into the patient at that position where subcutaneous injection is to take place until the locating surface is in juxtaposition with the skin surface while maintaining the positive location between the needle and the locating surface to insure that the sharpened end of the needle is located within the subcutaneous fat layer, and finally attaching the needle and locating surface to the patient to keep them in place. The method may also include using an injection needle with a right angle bend therein to define a locating section and a penetrating section adjacent the sharpened end with the penetrating section generally normal to the locating section, and the locating surface is defined by a locator pad; and affixing the locating section on the needle with respect to the locating surface so that it is generally parallel to the locating surface.

These and other features and advantages of the invention disclosed herein become more apparent upon consideration of the following detailed description and accompanying drawings wherein like characters of reference designate corresponding parts throughout the several views and in which:

BRIEF DESCRIPTION OF THE DRAWINGS

FIG. 1 is a perspective view illustrating a first embodiment of the invention;

FIG. 2 is another perspective view of the invention seen in FIG. 1;

FIG. 3 is an enlarged cross-sectional view taken along line 3—3 in FIG. 1 and showing the invention in use;

FIG. 4 is a perspective view illustrating a second embodiment of the invention in packaged condition;

FIG. 5 is a perspective view of the invention of FIG. 4 with the packaging removed;

FIG. 6 is an enlarged cross-sectional view taken along line 6—6 in FIG. 5;

FIG. 7 is a perspective view of the invention of FIG. 5 unfolded for use;

FIG. 8 is an enlarged cross-sectional view taken along line 8—8 in FIG. 7;

FIG. 9 is a perspective view of a third embodiment of the invention; and

FIG. 10 is an enlarged cross-sectional view taken along line 10-10 in FIG. 9.

These figures and the following detailed description disclose specific embodiments of the invention; however, it is to be understood that the inventive concept is not limited thereto since it may be embodied in other forms.

DETAILED DESCRIPTION OF ILLUSTRATIVE EMBODIMENTS

The invention disclosed in the figures of the drawings is designed to inject fluids into the subcutaneous fat layer of a patient by injecting the fluid to a known depth below the patient's skin to eliminate the trial and error technique required by the prior art. FIGS. 1-3 illustrate a first embodiment of the subcutaneous needle injection assembly of the invention designated 10, FIGS. 4-8 illustrate a second embodiment designated 110, and FIGS. 9 and 10 illustrate a third embodiment designated 210.

As seen in FIGS. 1-3, the subcutaneous needle injection assembly 10 includes generally an injection needle 11 and a locator pad 12. The needle 11 defines a fluid passage 15 therethrough from its inlet end 16 to its sharpened outlet end 18. The sharpened outlet end 18 punctures the patient's skin to allow the needle 11 to be inserted into the subcutaneous fat layer as will become more apparent. The injection needle 11 has a right angle bend 19 in it to form a locating section 20 about axis $A_{LS}$ adjacent the inlet end and a penetrating section 21 about axis $A_{PS}$ adjacent the sharpened outlet end 18 with the penetrating section 21 oriented about normal to the locating section 20. The inlet end 16 of needle 11 is connected to an appropriate fluid supply source FSS schematically seen in FIG. 3 such as an injection device via tubing T.

The locator pad 12 may have a variety of configurations and is illustrated as having a generally rectilinear base 25 defining a generally flat locating surface 26 on the underside thereof. The pad 12 is usually made of a resilient material such as plastic so that it will be comfortable to wear. The locating surface 26 will be in juxtaposition with the patient's skin when installed as illustrated in FIG. 3. An integral needle mount 28 is formed on the top of base 25 to hold needle 11 in place.

Needle 11 is positioned on pad 12 so that the locating section 20 extends through mount 28 with its axis $A_{LS}$ generally parallel to the locating surface 26. The penetrating section 21 extends through base 25 so that it projects outwardly from surface 26 generally normal thereto. The base 25, then, keeps the penetrating section 21 on needle 11 normal to the surface 26. The length of the penetrating section 21 on needle 11 is selected so that the sharpened outlet end 18 projects from surface 26 a prescribed distance $d_a$ seen in FIG. 3. The distance $d_a$ is selected to be slightly less than the distance $d_{MN}$ the subcutaneous fat layer/muscle interface is located below the skin surface at the likely encountered minimum thickness of the subcutaneous fat layer in the patient. While this minimum thickness may vary between different parts of the patient's body, this minimum thickness is about the same between corresponding parts of different patients' bodies. Thus, different distances $d_a$ may be provided for subcutaneous injection into different parts of the body but would normally not have to be different for different patients even though the thickness of the patients' subcutaneous fat layers may vary widely above this minimum thickness. This insures that the point of fluid injection will always be located sufficiently far from the puncture in the skin to isolate the point of injection from any skin surface irritation while, at the same time, preventing injection of the fluid into the muscle tissue of the patient.

As seen in FIG. 2, a separable needle cover 30 may be provided to fit over the projecting penetrating section 21 of needle 11 to keep it sterile prior to use. The cover 30 would, of course, be removed prior to use.

To reduce the likelihood of infection and irritation of the point where the skin is punctured, an antimicrobal substance M such as Betadine Jelly may be provided around the penetrating section 21 of needle 11 as seen in FIGS. 2 and 3. Preferably, the antimicrobal substance M is in a preformed annulus 32 around the penetrating section 21 of needle 11 at its juncture with the locating surface 26 on pad 12 as seen in FIG. 2 so that the substance M is always in place for use and seals the puncture P in the skin around the needle 11. An enlarged section 31 may be formed in the needle cover 32 as seen in FIG. 2 to accommodate the preformed antimicrobal substance M.

Once the penetrating section 21 of needle 11 is exposed, the assembly 10 is installed by simply pressing it into place keeping the locating surface 26 generally parallel to the skin surface. After the assembly 10 has been pressed in place, a piece of tape 34 seen in FIG. 3 is usually applied to keep the assembly 10 in place. This insures that the penetrating section 21 is normal to the skin surface while minimizing the relative movement between the skin and needle 11 at puncture P to reduce irritation.

As seen in FIGS. 4-8, the subcutaneous needle injection assembly 110 includes generally an injection needle 111 and a locator pad 112. The needle 111 is like needle 11 with inlet end 116 and sharpened outlet end 118. The injection needle 111 has a right angle bend in it to form the locating section adjacent the inlet end and the penetrating section 121 adjacent the sharpened outlet end 118 with the penetrating section 121 oriented about normal to the locating section. The inlet end 116 of needle 111 is connected to an appropriate fluid supply source via tubing T.

The locator pad 112 has a base 125 with a needle mount 128 to hold needle 111 in place. Unlike pad 12, however, the base 125 can be folded down around the penetrating section 121 on needle 111 to cover it. When unfolded, as seen in FIG. 8, the base 125 corresponds in shape to base 25 and defines the flat locating surface 126 about the penetrating section 121 of needle 111. The base 125 is hinged generally along lines 135 on opposite sides of the needle mount 128 as seen in FIGS. 5 and 6 so that the base 125 has an effective fold axis $A_F$ in registration under the axis of the locating section of the needle 111. While different hinging constructions may be used, the construction illustrated has grooves 136 formed in the top side of the base 125. Because base 125 is made of a resilient material such as plastic, this forms a living hinge section 138 along the bottom of each of the grooves 136 as best seen in FIG. 6 so that the outboard sections 139 on base 125 on opposite sides of the fold axis $A_F$ can be folded down over the penetrating end 121 of needle 111 as seen in FIG. 6. The outer edges of sections 139 are in juxtaposition so as to seal the penetrating end 121 of needle 111 therebetween as seen in FIGS. 5 and 6 to keep it sterile prior to use. Tabs 140 may be provided on sections 139 to facilitate unfolding them prior to use.

The microbal substance M is prepackaged around the penetrating end 121 of needle 111 as seen in FIG. 6. When the sections 139 are unfolded as seen in FIG. 8, the substance M is exposed for use as already explained.

Appropriate packaging 141 (FIG. 4) may be provided to maintain the sections 139 folded. The packaging 141 is stripped away prior to use using grip strips 142 also seen in FIG. 4.

The installation of the injection assembly 110 after it is unfolded is the same as that discussed for assembly 10. Thus, the depth of injection is positively controlled.

As seen in FIGS. 9 and 10, the subcutaneous needle injection assembly 210 also includes generally an injection needle 211 and a locator pad 212. Additionally, a penetration adjustment mechanism 114 is provided to control the amount of exposure of needle 211 as will become more apparent. The needle 211, like needle 11, defines a fluid passage therethrough from its inlet end 216 to its sharpened outlet end 218. The injection needle 211 also has a right angle bend 219 in it to form locating section 220 adjacent the inlet end and penetrating section 221 adjacent the sharpened outlet end 218 with the penetrating section 221 oriented about normal to the locating section 220. The inlet end 216 of needle 211 is also connected to an appropriate fluid supply source via tubing T.

The locator pad 212 corresponds generally to pad 12 with a generally rectilinear base 225 defining a generally flat locating surface 226 on the underside thereof which will be in juxtaposition with the patient's skin when installed. An integral needle mount 228 is formed on the top of base 225 to hold needle 211 in place; however, needle mount 228 is short as compared with mount 28 and engages the locating section 220 of needle 211 adjacent its inlet end 216. This allows the bend 219 and penetrating section 221 of needle 211 to be raised or lowered with respect to the locating surface 226 on pad 212. The hole 250 in pad 212 through which penetrating section 221 passes keeps section 221 normal to surface 226.

The penetration adjustment mechanism 114 engages the locating section 120 of needle 211 adjacent bend 219 to positively control the distance $d_a$ the sharpened outlet end 218 projects from surface 226. Mechanism 114 includes a stepped adjustment member 251 which slides on the top of base 225. The steps on member 251 may be grooved as seen at 252 to keep the member 251 in place. Each groove 252 is located at a different height from the top of base 225 so that the penetration distance $d_a$ can be changed by shifting the needle 211 to different grooves 252 in member 251. Guides 254 may be provided to keep member 251 in place axially of section 220 on needle 211.

This allows the injection assembly 210 to be adjusted for use at different body positions. After adjustment is completed, the injection assembly 210 would be installed like injection assembly 10.

We claim:

1. An injection needle assembly connectable to the tubing from a fluid supply source for injecting fluids into the subcutaneous fat layer of a patient below the skin without penetrating the muscle tissue comprising:

an elongate injection needle defining a fluid passage therethrough, said injection needle having an inlet end to be connected to the tubing from the fluid supply soure and a sharpened outlet end opposite the inlet end adapted to puncture the patient's skin and subcutaneous fat layer, said needle defining a right angle bend therein forming a locating section on said needle adjacent the inlet end thereof and a penetrating section on said needle adjaclent the sharpened outlet end thereof oriented normal to said locating section;

a locator pad having opposed top and bottom surfaces, said bottom surface adapted to lie against the patient's skin; and a needle mount integral with said locator pad on the top surface thereof, said needle mount enclosing said locating section and said right angle bend of said needle so that said locating section of said needle lies along said top surface of said locator pad generally parallel to said bottom surface and said inlet end of said needle projecting from said needle mount parallel to said bottom surface for connection to the tubing, said penetrating section of said needle extending through said locator pad and projecting from said bottom surface, said needle mount and said locator pad maintaining said needle fixed with respect to said bottom surface and said penetrating section fixed normal to said bottom surface with said sharpened outlet and located a prescribed distance from said surface to positively control the depth of penetration of said sharpened outlet end of said needle into the subcutaneous fat layer of the patient when said bottom surface is in juxtaposition with the patient's skin.

2. The injection needle assembly of claim 1 further including an antimicrobal substance around said penetrating section of said needle at said bottom surface so that said antimicrobal substance is placed in operative cooperation with the puncture in the patient's skin made by said needle.

3. The injection needle assembly of claim 2 further including needle cover means for selectively covering said penetrating section of said needle prior to use to maintain said penetrating section of said needle sterile.

4. The injection needle assembly of claim 1 wherein said locator pad is constructed and arranged so that said locator pad is foldable about a fold axis generally coaxial with said locating section of said needle whereby those portions of said locator pad on opposite sides of said fold axis can be folded over said penetrating section of said needle to cover same and alternately unfolded from around said penetrating section of said needle to expose same for use.

5. An injection needle assembly connectable to tubing from a fluid supply source for injecting fluids into the subcutaneous fat layer of a patient below the skin without penetrating the muscle tissue comprising:

an elongate injection needle defining a fluid passage therethrough, said injection needle having an inlet end to be connected to the tubing from the fluid supply source and a sharpened outlet end opposite the inlet end adapted to puncture the patient's skin and subcutaneous fat layer, said needle defining a right angle bend therein forming a locating section on said needle adjacent the inlet end thereof and a penetrating section on said needle adjacent the sharpened outlet end thereof oriented normal to said locating section;

a locator pad having opposed top and bottom surfaces, said bottom surface adapted to lie against the patient's skin;

a resilient needle mount integral with said locator pad on the top surface thereof enclosing a portion of said locating section of said needle adjacent the inlet end thereof so that said locating section extends over the top surface of said locator pad, said locator pad defining a hole therethrough slidably receiving said penetrating section of said needle therethrough so that said penetrating section of said needle projects from the bottom surface and is maintained generally normal thereto; and an adjustment mechanism engaging said locating section of said needle adjacent said bend to selectively raise and lower said locating section adjacent said bend while said resilient needle mount flexes to permit movement of said bend and said penetrating section of said needle yet retains the inlet end of said needle closely adjacent the top surface of said locator pad so that the distance the sharpened outlet end of said needle projects from the bottom surface of said locator pad can be changed to change the depth of penetration of said sharpened outlet end of said needle into the subcutaneous fat layer of the patient when said bottom surface is in juxtaposition with the patient's skin.

6. The injection needle assembly of claim 5 wherein said adjustment mechanism includes a slide member slidably mounted on the top surface of said locator pad for movement generally transversely of said needle, said slide member defining a plurality of steps thereon located at different heights from the top surface of said locator pad and movable between the top surface of said locator pad and said locating section of said needle adjacent said bend to change the depth of penetration of said sharpened outlet end of said needle.

* * * * *